(12) United States Patent
Temeles (10) Patent No.: US 6,283,971 B1
(45) Date of Patent: Sep. 4, 2001

(54) EXPANDABLE ACETABULAR REAMING SYSTEM

(76) Inventor: Randy S. Temeles, 10 Floral Dr., Wheeling, WV (US) 26003

( * ) Notice: Subject to any disclaimer, the term of this patent is extended or adjusted under 35 U.S.C. 154(b) by 0 days.

(21) Appl. No.: 09/558,281

(22) Filed: Apr. 25, 2000

(51) Int. Cl.$^7$ .................................................. A61B 17/14
(52) U.S. Cl. .............................................. 606/81; 606/79
(58) Field of Search .................................. 606/80, 81, 79

(56) References Cited

U.S. PATENT DOCUMENTS

| | | |
|---|---|---|
| 3,702,611 | 11/1972 | Fishbein . |
| 4,782,833 | 11/1988 | Einhorn et al. . |
| 5,299,893 | 4/1994 | Salyer et al. . |
| 5,462,548 * | 10/1995 | Pappas et al. .......................... 606/80 |
| 5,830,215 | 11/1998 | Incavo et al. . |
| 5,919,195 | 7/1999 | Wilson et al. . |
| 5,925,056 | 7/1999 | Thomas et al. . |

* cited by examiner

*Primary Examiner*—Paul J. Hirsch
*Assistant Examiner*—Michael B. Priddy
(74) *Attorney, Agent, or Firm*—Dale J. Ream (57) ABSTRACT

An expandable acetabular reaming system for use in hip replacement surgery comprises a reamer head having a convex forward surface attached to a base plate that defines an interior space therebetween. The forward surface includes a plurality of apertures therethrough. The base plate includes a central aperture over which a flexible bladder is mounted within the interior space. The reaming system further includes a plurality of cutting blades mounted to the bladder and positioned so as to correspond with respective apertures. An air cylinder is coupled to the underside of the base plate and includes an open top in communication with the bladder through the central aperture of the base plate. A threaded shaft extends through a threaded aperture in a bottom wall of the air cylinder and is coupled to a thimble-type knob. As a user turns the knob, the shaft rotates to force air through the base plate aperture so as to inflate the bladder. Turning the knob in an opposite direction deflates the bladder in like manner. The blades are projected through respective apertures as the bladder is inflated and are retracted as the bladder is deflated.

19 Claims, 8 Drawing Sheets

EXPANDABLE ACETABULAR REAMING SYSTEM

BACKGROUND OF THE INVENTION

This invention relates generally to reaming systems and, more particularly, to an expandable reaming system for reaming an acetabulum in preparation for implanting a prosthetic component, such as an acetabular cup or socket.

Acetabular hip surgery involves reforming the normal hip socket, or acetabulum, so that a proper bearing surface for the ball of the femur is established and which will support normal motion of the leg. The acetabulum needs to be shaped so that it can receive a metallic or plastic artificial socket. To ensure a proper fit of the artificial socket, deteriorated or diseased bone is cut away until healthy bone becomes visible. Typically, reamer heads of increasingly larger size are required as bone is cut away and the socket is enlarged. Each time a larger reamer head is needed, the reaming system must be removed from the patient's acetabulum, the reamer head is removed from the drive shaft of the surgical drill, and the next larger reamer head is attached thereto. This sequence may be repeated several times until the acetabulum is completely prepared to receive an acetabular prosthetic implant.

Several types of acetabular reamer heads are known in the art. Further, a surgical expansive reamer for hip sockets is taught in U.S. Pat. No. 3,702,611. Having to swap reamer heads multiple times during a hip surgery, as discussed above, is inconvenient, inefficient, and may even lead to surgical errors in that the angle of acetabular penetration cannot be accurately preserved during reamer head substitutions. Further, the '611 reamer is also inefficient in that it requires the acetabulum to be prepared with another instrument prior to its use and does not include a satisfactory mechanism for accurate incremental expansion of the reamer.

Therefore, it is desirable to have a reaming system which can be used to prepare an acetabulum to receive an artificial socket without having to substitute one reamer head for another. It is further desirable to have a reaming system having a reamer head which is manually expandable to a plurality of desired sizes.

SUMMARY OF THE INVENTION

An expansible acetabular reaming system according to a preferred embodiment of the invention includes a reamer head having a convex forward surface and a base plate which together form an interior space therebetween. The forward surface includes a plurality of spaced apart apertures extending therethrough. The base plate also includes a central aperture. A flexible bladder is mounted within the interior space of the reamer head and is sealed around the central base plate aperture. The bladder is concentric to the generally hemispherical shape of the forward surface and, even when inflated, is spaced apart therefrom. A plurality of cutter blades are fixedly attached to the bladder and extend outwardly therefrom. The blades are spaced apart from one another and are positioned to correspond to respective apertures in the convex surface.

An air cylinder depends from the base plate of the reamer head and includes an open top positioned immediately adjacent the central aperture of the base plate for communicating the bladder with the air cylinder. The air cylinder includes a bottom wall having a threaded bore through which a threaded shaft extends. The end of the threaded shaft which extends from the air cylinder is coupled to a thimble-type knob. A disc-like platform is attached to the opposing shaft end within the air cylinder. Therefore, as the knob is turned in a first direction by a user, the shaft is threadably rotated so as to force air within the cylinder into the bladder. As the bladder is inflated, the blades are projected through respective corresponding apertures in the convex forward surface. Conversely, as the knob is turned in an opposing direction thereby deflating the bladder, the blades are retracted through the apertures.

Scale indicia are provided on the exterior of the air cylinder housing such that the blades may be extended or retracted to particular positions during a hip replacement surgical operation. This expandability is significant in that traditional hip replacement surgeries require the use of multiple acetabular reaming heads of increasingly larger sizes. According to the present invention, the effective size of the reamer head may be adjusted as desired without needing to remove the head from the acetabulum; instead adjustment may be accomplished by turning the knob to the desired size as indicated by the scale. Even if the reamer head is removed from the acetabulum, adjustment can be made quickly as the reamer head need not be removed and replaced. The reaming system includes a socket adapted to be removably attached to the drive shaft of a surgical drill.

Therefore, a general object of this invention is to provide a reaming system which can completely prepare an acetabulum to receive an artificial socket without having to substitute one reamer head for another.

Another object of this invention is to provide a reaming system, as aforesaid, which reduces the amount of time required to conduct an acetabular hip replacement surgery.

Still another object of this invention is to provide a reaming system, as aforesaid, having a plurality of blades which project or retract through a reamer head according to a desired reamer head size.

Yet another object of this invention is to provide a reaming system, as aforesaid, in which the degree of projection or retraction of the reaming blades is manually controlled by user actuation of an air bladder.

A further object of this invention is to provide a reaming system, as aforesaid, having a reservoir within the reamer head which can collect bone and viscous fluids.

A still further object of this invention is to provide a reaming system, as aforesaid, having a reamer head which can be expanded in ½ mm increments.

Other objects and advantages of this invention will become apparent from the following description taken in connection with the accompanying drawings, wherein is set forth by way of illustration and example, embodiments of this invention.

BRIEF DESCRIPTION OF THE DRAWINGS

FIG. 3a is a front view of the reaming system as in FIG. 2a;

FIG. 6 is a sectional view of the reaming system taken from line 6—6 of FIG. 3a;

DESCRIPTION OF THE PREFERRED EMBODIMENT

Figure 1:
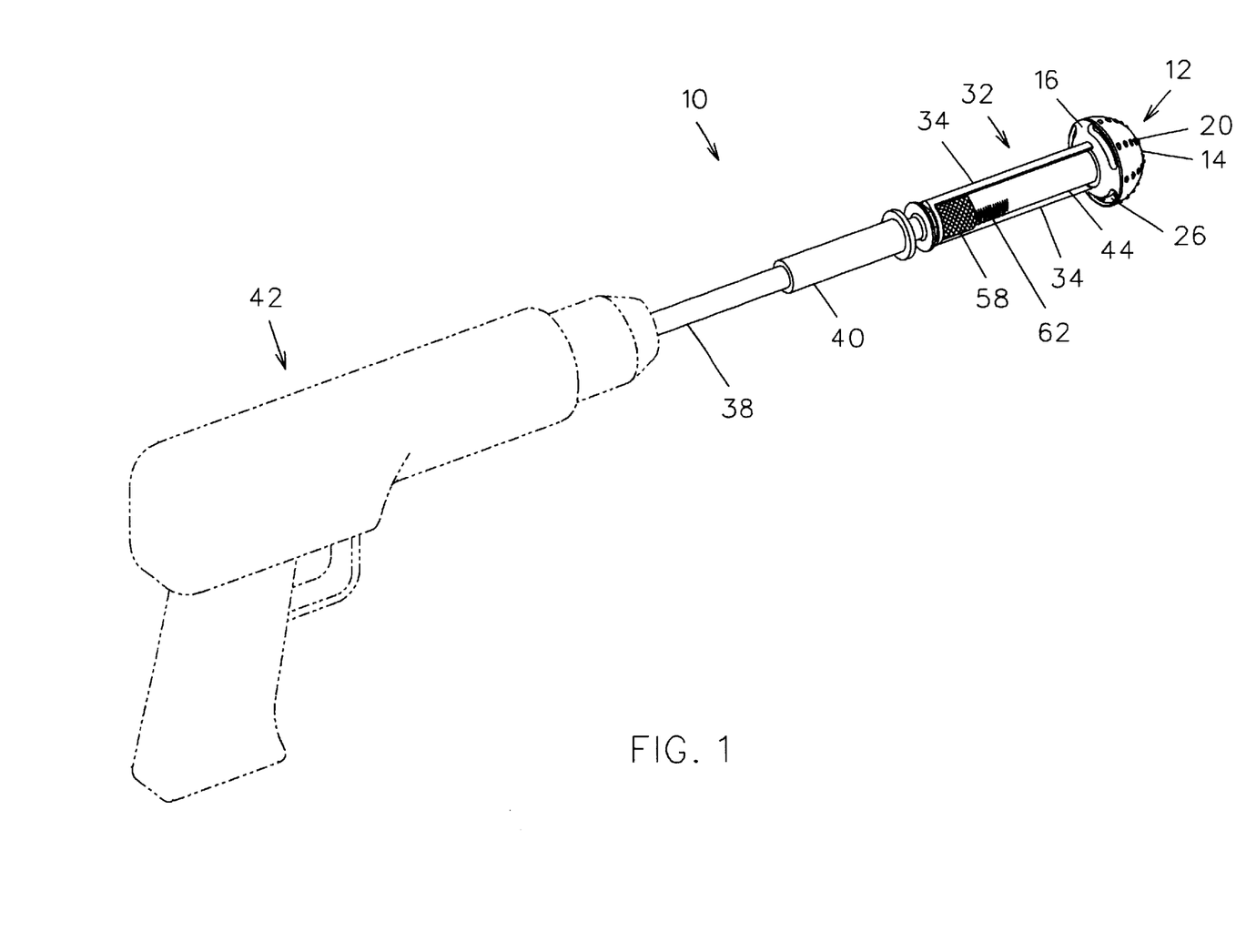
FIG. 1 is a perspective view of the reaming system coupled to a surgical drill.
Figure 2A:
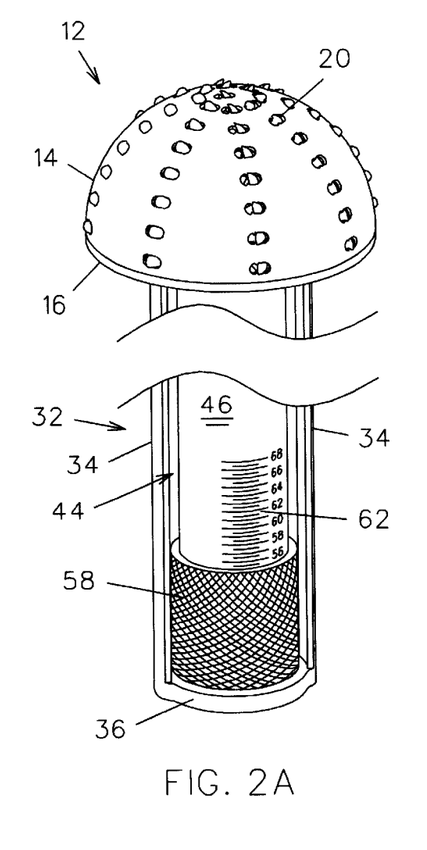
FIG. 2a is a perspective view of the reaming system with the blades in a fully retracted configuration.
Figure 2B:
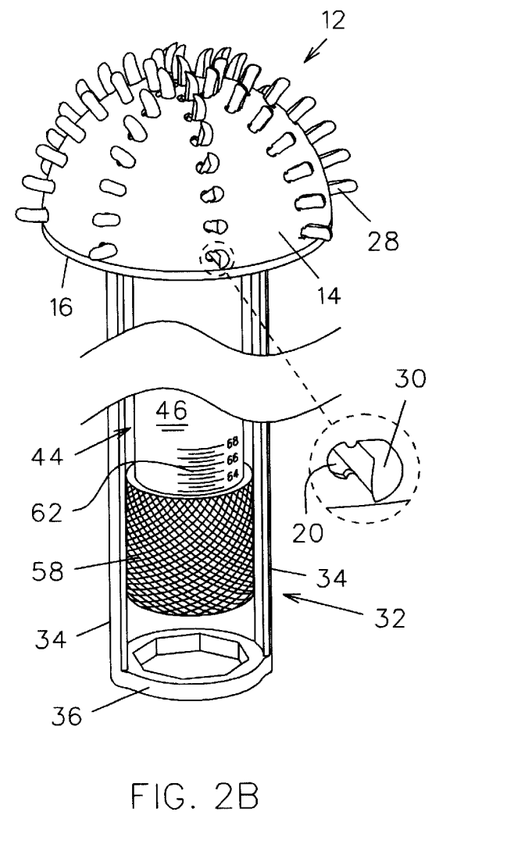
FIG. 2b is a perspective view of the reaming system with the blades in a fully extended configuration and with an isolated view on an enlarged scale of a cutting blade.
Figure 3A:
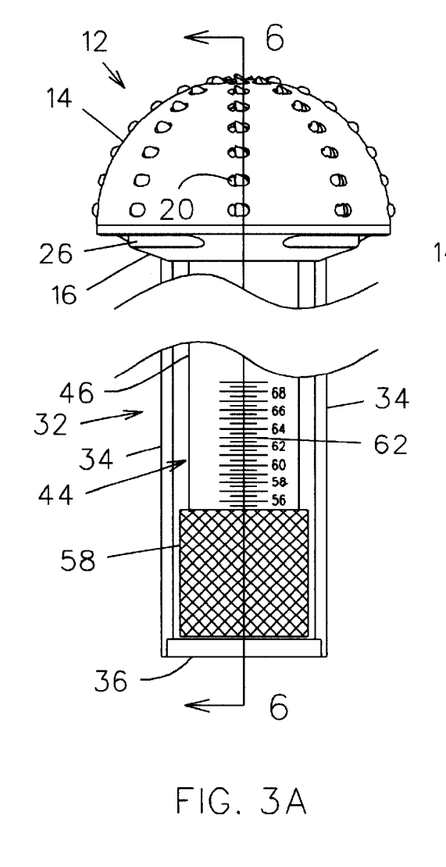
Figure 3B:
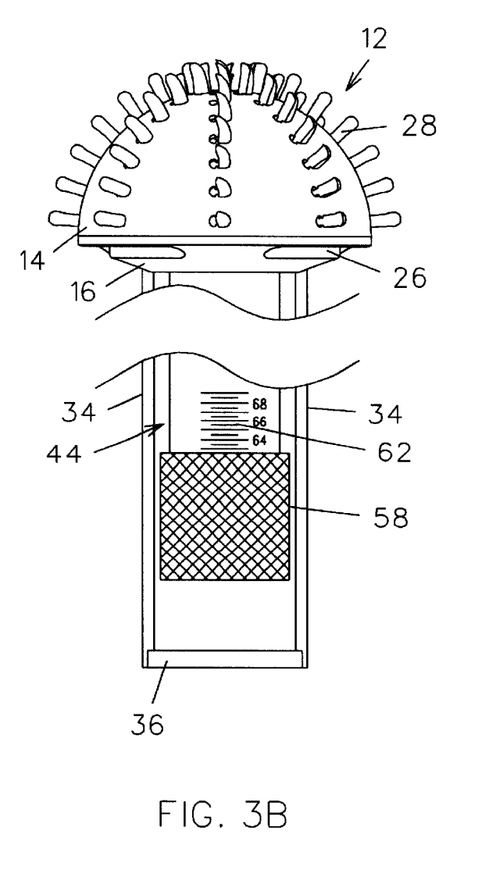
FIG. 3b is a front view of the reaming system as in FIG. 2b.
Figure 4:
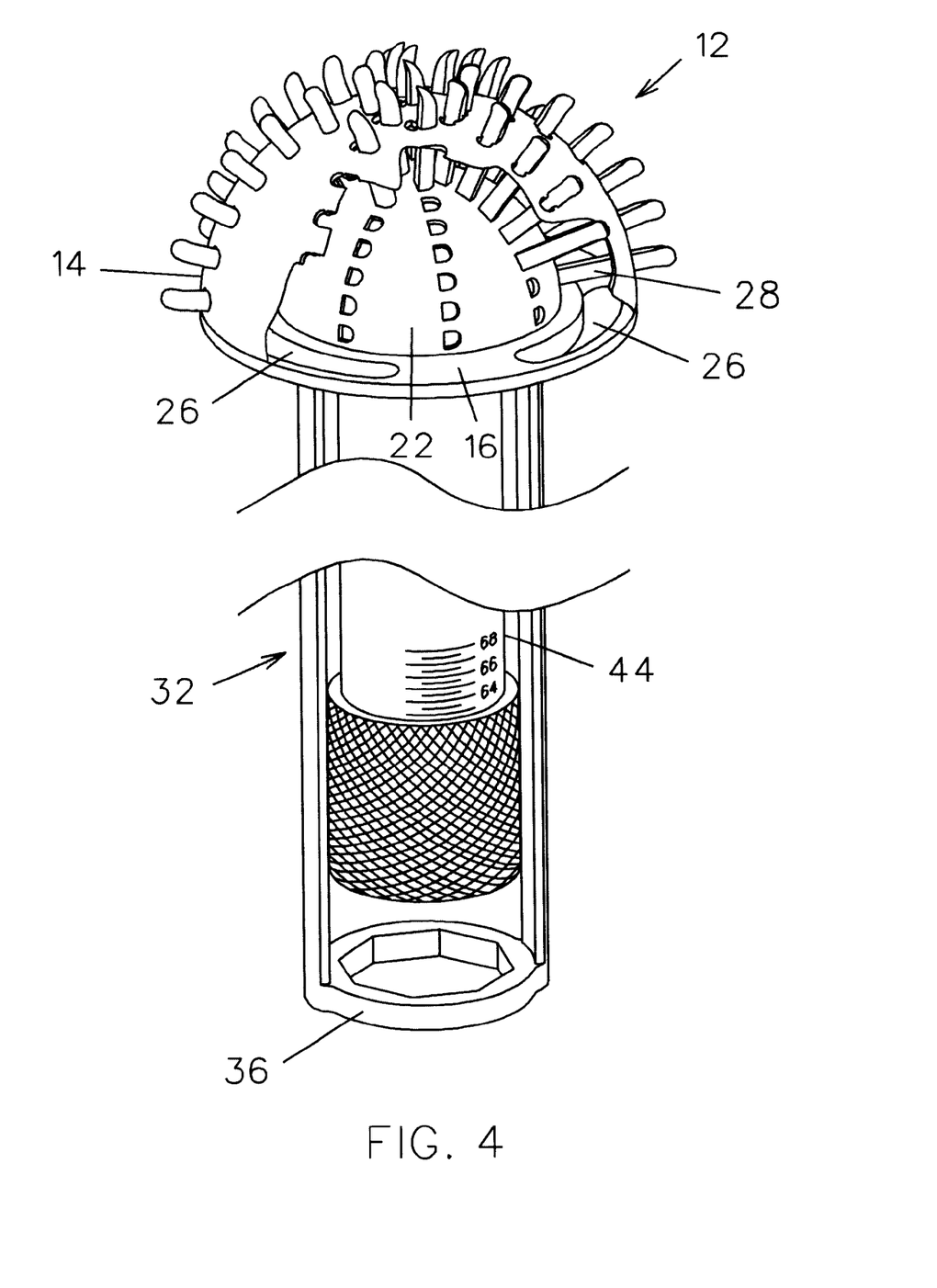
FIG. 4 is a perspective view of the reaming system as in FIG. 2b on an enlarged scale having a portion of the reamer head cut away.
Figure 5:
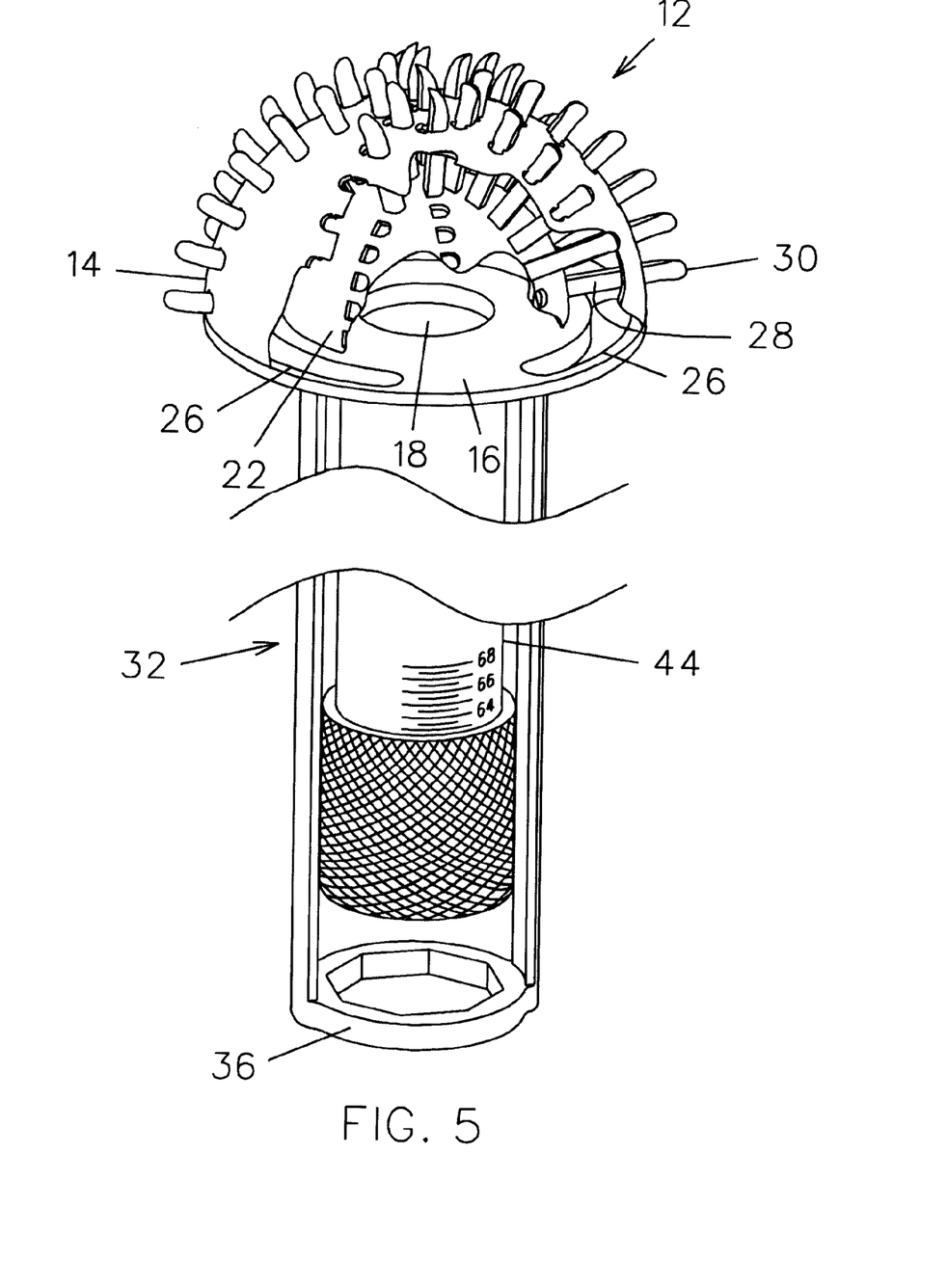
FIG. 5 is a perspective view of the reaming system as in FIG. 2b on an enlarged scale having portions of the reamer head and bladder cut away.

An expandable reaming system 10 according to a preferred embodiment of the present invention will now be described with reference to FIGS. 1–6 of the drawings. The reaming system 10 comprises a reamer head 12 having a generally hemispherical convex forward surface 14 integral to a base plate 16 which closes the bottom thereof (FIG. 5). Therefore, an interior space is formed within the reamer head 12. The reamer head 12 is constructed of stainless steel although a durable plastic material would also be suitable. The base plate 16 includes a central aperture 18 (FIG. 5) while the forward surface 14 includes a plurality of spaced apart apertures 20 therethrough (FIG. 2a). Each aperture 20 through the forward surface 14 is configured to guide a cutting blade 28 therethrough, as to be more fully described below.

Figure 6:
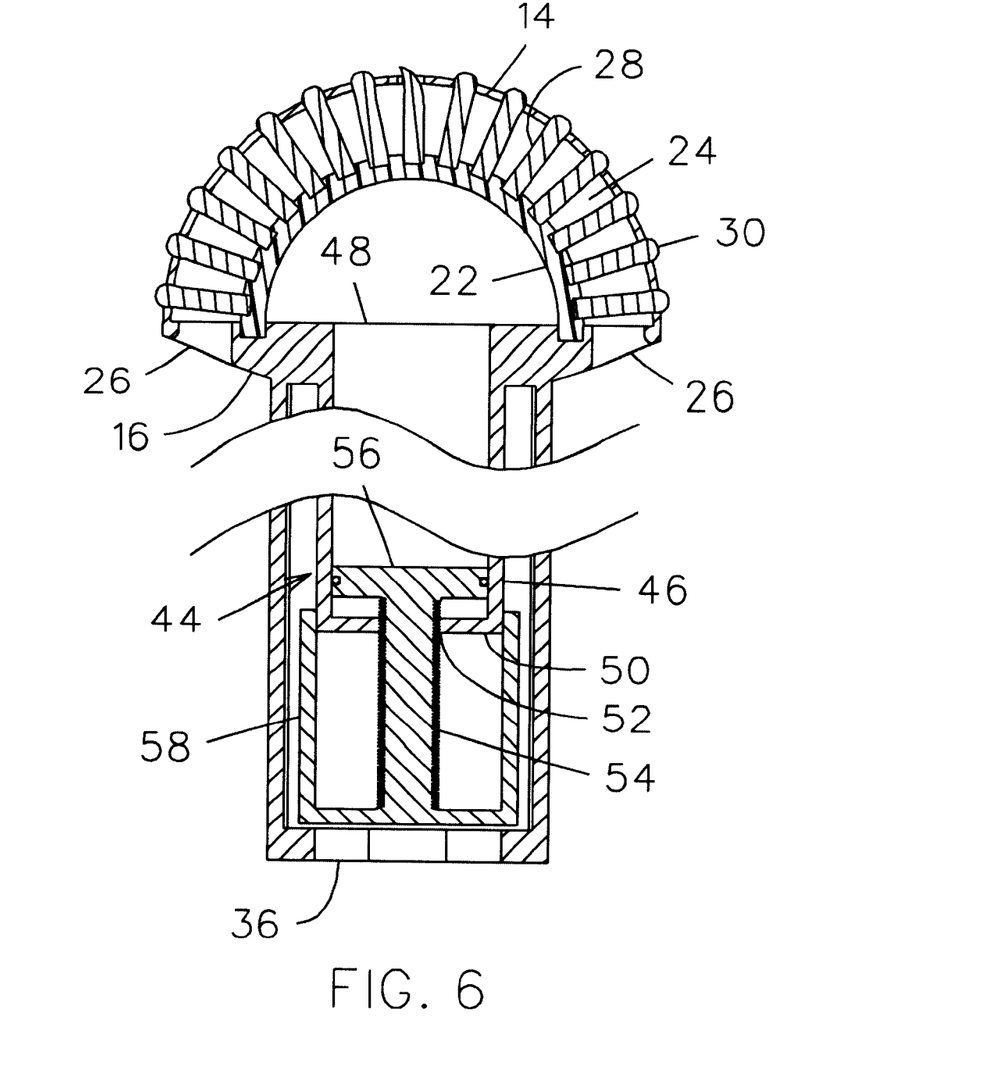

The reamer head 12 further includes a bladder 22 fixedly attached to the base plate 16 within the interior space of the reamer head 12. Edges of the bladder 22 are sealed to the base plate 16 around the central aperture 18 such that air within the bladder 22 cannot escape therefrom. The bladder 22 is constructed of rubber or other suitable flexible material. The bladder 22 presents a configuration concentric to the forward surface 14 but is spaced apart therefrom, whether the bladder is inflated or deflated. This space between the bladder 22 and the forward surface 14 forms a reservoir 24 for collecting bone fragments and other viscous waste during a surgical reaming procedure (FIG. 6). Spaced apart slots 26 extending through the base plate 16 adjacent radial edges thereof allow for the removal of the surgical waste materials from the reamer head 12 (FIGS. 4–5).

A plurality of cutting blades 28 are fixedly attached to the bladder 22 and project therefrom through the interior space of the reamer head 12. Each blade 28 is positioned to correspond with one of the apertures 20 in the forward surface 14 and configured to project therethrough upon inflation of the bladder 22, as to be more fully described later. The free end 30 of each blade includes a sharpened edge and a cup-like configuration suitable for cutting bony material and scooping the cut material through a respective aperture 20 and into the reservoir 24.

The reaming system 10 further includes a neck or framework 32 having a pair of support members 34 depending from the base plate 16 opposite the forward surface 14 of the reamer head 12. A socket 36 is integrally attached to the distal ends of the support members 34 relative to the reamer head 12, the socket 36 being configured to be snappably coupled to the drive shaft 38 of a surgical drill 42. The drive shaft 38 may include a handle 40 pivotally coupled thereto such that the handle 40 may be grasped by the surgeon for guiding the reamer head 12 without the handle 40 itself being rotated by the drive shaft 38.

An air cylinder 44 depends from the base plate 16 and extends within the framework 32. As best shown in FIGS. 3a and 6, the air cylinder 44 comprises a tubular housing 46 having an open top 48 and a closed bottom wall 50. The air cylinder 44 is positioned such that the open top 48 is immediately adjacent the central aperture 18 of the base plate 16 such that the bladder 22 is in communication with the air cylinder 44. The bottom wall 50 includes a threaded aperture 52 through which a threaded shaft 54 extends. A disc-like platform 56 is fixedly attached to a first end of the shaft 54 within the tubular housing 46, the platform 56 providing an air seal relative to air above and below it. An opposed end of the shaft 54 is integrally attached to a thimble-like knob 58, the knob and shaft combination also referred to as a micrometer screw. The shaft 54 is completely contained within the knob 58 and the knob 58 includes an open top having a diameter greater than a diameter of the tubular housing 46 such that the knob 58 is free to pivot about the housing 46 as the shaft 54 is rotated therein. Markings indicative of a scale 62 are included on the housing 46 in ½ mm increments such that the position of the knob 58 relative to the scale 62 indicates the present size of the reamer head 12.

In use, the socket 36 is snappably coupled to the end of the drive shaft 38 of a surgical drill 42. Initially, the knob 58 is rotated such that the platform 56 bears against the bottom wall 50 of the air cylinder 44. This action draws air out of and thus deflates the bladder 22. In other words, with the platform 56 at its lowest or most rearward position, the volume of the air cylinder 44 is at its greatest causing the air pressure within the bladder 22 to be at its lowest level. As the bladder 22 is deflated, the blades 28 mounted thereto are retracted into the reservoir 24. The reamer head 12 can now be easily positioned within the acetabulum of a surgical patient.

The knob 58 may now be rotated in an opposite direction such that the threaded shaft 54 moves the platform 56 forward within the air cylinder 44. As the platform 56 is moved forward, it pushes air through the open top of the air cylinder and the central aperture 18 of the base plate 16 and into the bladder 22. As the bladder 22 is incrementally inflated, the blades 28 are projected through corresponding apertures 20 in the forward surface 14. The blades 28 may be projected incrementally in this manner until the knob 58 registers a desired size marking on the scale 62. Further incremental inflation of the bladder 22 may be made in this manner each time a larger reamer head size is needed. When the surgery is complete, or any time the surgeon desires to remove the reamer head 12 from the acetabulum, the bladder 22 may be slightly deflated to facilitate easy removal and to avoid damage to the reformed acetabulum.

Figure 7:
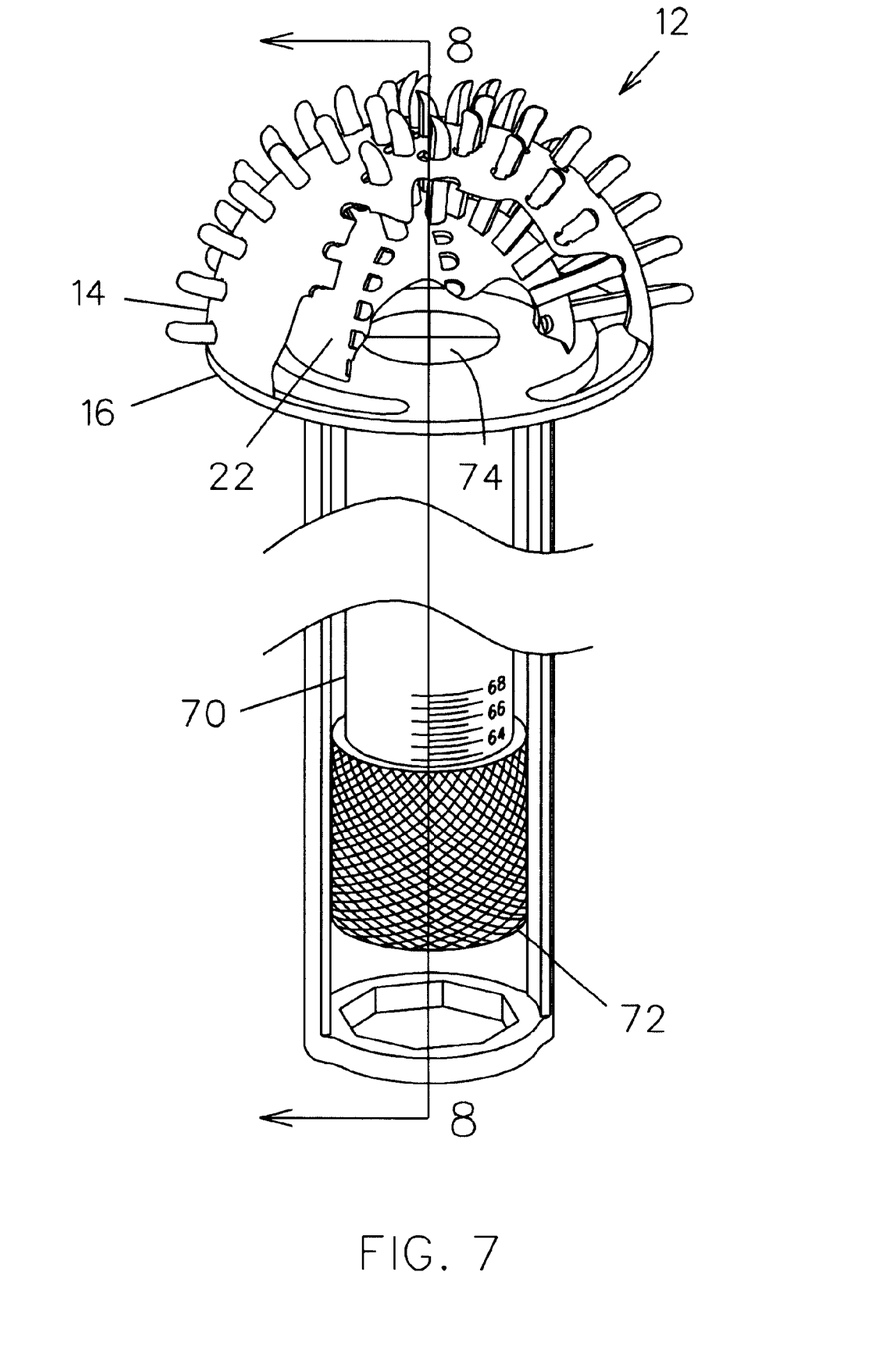
FIG. 7 is an alternative embodiment of the reaming system having portions of the reamer head and bladder cut away.
Figure 8:
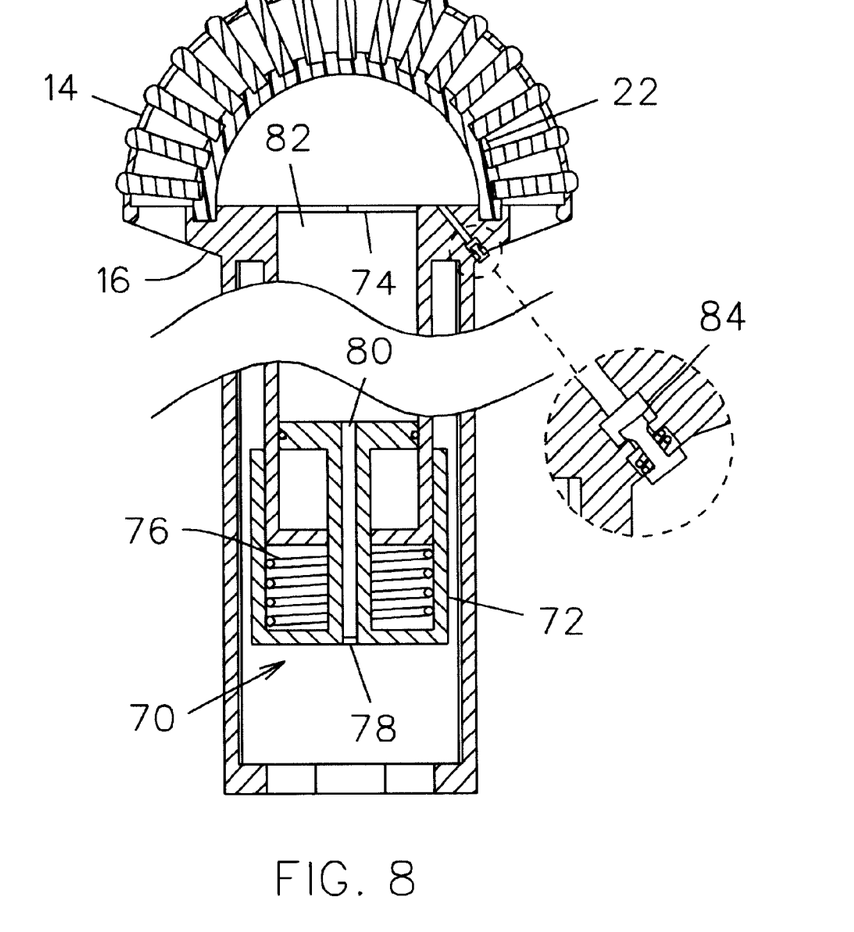
FIG. 8 is a sectional view of the alternative embodiment of the reaming system taken along line 8—8 of FIG. 7.

An alternative embodiment of the reaming system is shown in FIGS. 7 and 8 and is identical to the reaming system 10 described above except as specifically noted below. In the alternative embodiment, the bladder 22 may be incrementally inflated with a spring-loaded piston pump 70 which depends from the base plate 16 rather than an air cylinder 44. When a pump 72 is moved forward, springs 74 are compressed and air is forced through a valve 74 into the bladder 22. Following pump depression, the springs 76 return to their unbiased or non-compressed state, drawing air through another valve 78 into an air channel 80 and reservoir 82. Repeated depressions of the pump 72 incrementally inflate the bladder 22 in like manner. A relief valve 84 extends from the bladder 22 for manual deflation thereof.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A surgical cutting tool, comprising:
    a cutter head having a convex surface and a plurality of apertures extending through said surface;
    a flexible bladder mounted within said cutter head and spaced apart from said convex surface;
    a plurality of cutter blades attached to said bladder, each blade positioned to correspond with a respective one of said apertures; and
    means for selectably inflating or deflating said bladder, whereby said blades extend incrementally through said respective apertures as said bladder is inflated and retract incrementally through said respective apertures as said bladder is deflated.

2. A surgical cutting tool as in claim 1 wherein said cutter head further comprises a base plate fixedly attached to a peripheral edge of said convex surface for forming an interior space within said cutter head, said base plate having an aperture therethrough for communicating said inflating or deflating means with said bladder.

3. A surgical cutting tool as in claim 1 wherein said bladder is spaced apart from said convex surface so as to form a reservoir adapted to collect surgical waste material during use of the cutting tool.

4. A surgical cutting tool as in claim 1 wherein said inflating or deflating means comprises an air cylinder coupled to said cutter head, said air cylinder having an open top in communication with said bladder and a shaft threadably movable within said cylinder, whereby said bladder is incrementally inflated upon a movement of said shaft in one direction and incrementally deflated upon a movement of said shaft in another direction.

5. A surgical cutting tool as in claim 1 wherein said inflating or deflating means is a piston pump coupled to said cutting head, said pump including:
    an outlet valve in communication with said bladder;
    an actuator means for selectably delivering a predetermined amount of air through said outlet valve into said bladder; and
    a relief valve for selectably releasing air from said bladder.

6. A surgical cutting tool as in claim 1 wherein said blades include a cupped configuration adapted to cut and scoop bone material away from the surgical site.

7. An acetabular reaming system for use in hip replacement surgery, comprising:
    a reamer head having a convex forward end attached to a base plate defining an interior space therebetween, said forward end having a plurality of apertures extending therethrough;
    a bladder mounted to said base plate within said interior space, said bladder being concentric to and spaced from said forward end of said reamer head so as to form a reservoir adapted to collect surgical waste material;
    a plurality of cutter blades mounted to said bladder, each blade positioned thereon in correspondence with one of said apertures; and
    a tubular air cylinder depending from said base plate including an open top in communication with said bladder and a shaft movable within said cylinder adapted to incrementally inflate or deflate said bladder upon a movement of said shaft, whereby said blades are projected through said corresponding apertures when said bladder is incrementally inflated and said blades are retracted through said corresponding apertures when said bladder is incrementally deflated.

8. A reaming system as in claim 7 wherein said base plate includes a central aperture adapted to communicate said air cylinder with said bladder, said bladder being attached to said base plate in a sealed relationship about said central aperture whereby air delivered to said bladder from said air cylinder incrementally inflates said bladder.

9. A reaming system as in claim 7 wherein said base plate includes at least one slot positioned between said bladder and said forward end such that surgical waste material accumulated within said reservoir is removable therethrough.

10. A reaming system as in claim 7 wherein said blades include a cup-shaped configuration adapted to cut and scoop bone and viscous fluids away from the surgical site and into said reservoir.

11. A reaming system as in claim 7 wherein said air cylinder includes a bottom wall opposite said open top having a threaded aperture therethrough, said shaft extending through said bottom wall aperture and having threads complementary thereto, whereby said shaft is threadably movable within said air cylinder upon a user rotation of said shaft.

12. A reaming system as in claim 7 further comprising:
    a socket coupled to said base plate and spaced apart therefrom;
    a drive shaft having a forward end adapted to be coupled to said socket and a rearward end adapted to be rotated by a driver, whereby said reamer head is rotated upon a rotation of the driver when said drive shaft is coupled to said socket.

13. A reaming system as in claim 12 further comprising a handle pivotally coupled to said drive shaft, said handle adapted to be grasped for guiding said reaming head without itself being rotated by said drive shaft.

14. An acetabular reaming system for use in hip replacement surgery, comprising:
    a cutter head having a convex forward end attached to a base plate and defining an interior space therebetween, said forward end having a plurality of apertures extending therethrough;
    a framework having a pair of elongate support members depending from said base plate and having a socket extending between distal ends of said support members relative to said cutter head;
    a flexible bladder mounted within said interior space and spaced from said forward end of said cutter head so as to form a reservoir adapted to collect surgical waste material;
    a plurality of cutter blades attached to said bladder, each blade positioned to correspond with a respective one of said apertures;
    an air cylinder mounted to said base plate and extending within said framework, said base plate having a central aperture therethrough for communicating said air cylinder with said bladder;
    means for selectably actuating said air cylinder for incrementally inflating or deflating said bladder, whereby said blades extend incrementally through said respective apertures as said bladder is inflated and retract incrementally through said apertures as said bladder is deflated; and
    a drive shaft having a forward end adapted to be coupled to said socket and a rearward end adapted for rotation by a driver, whereby said cutter head is rotated upon a rotation by the driver when said forward end is coupled to said socket.

15. A reaming system as in claim 14 wherein said bladder is attached to said base plate in a sealed relationship about said central aperture whereby air delivered to said bladder from said air cylinder incrementally inflates said bladder.

16. A reaming system as in claim 14 wherein said base plate includes at least one slot positioned between said bladder and said forward end such that surgical waste material accumulated within said reservoir is removable therethrough.

17. A reaming system as in claim 14 wherein said blades have a cup-shaped configuration adapted to cut and scoop bone and viscous fluids away from the surgical site and into said reservoir.

18. A reaming system as in claim 14 wherein said air cylinder includes a tubular housing having an open top positioned adjacent said aperture in said base plate and a bottom wall opposite said open top, said bottom wall having a threaded aperture therethrough; and said actuating means including a shaft extending through said bottom wall aperture and having threads complementary thereto, whereby said shaft is threadably movable within said air cylinder upon a user rotation of said shaft so as to incrementally inflate or deflate said bladder.

19. A reaming system as in claim 14 further comprising a handle pivotally coupled to said drive shaft, said handle adapted to be grasped by a user for guiding said cutter head without itself being rotated by said drive shaft.

\* \* \* \* \*